US008030049B2

(12) United States Patent
Tzortzis et al.

(10) Patent No.: US 8,030,049 B2
(45) Date of Patent: Oct. 4, 2011

(54) GALACTOSIDASE WITH α-GALACTOSYLTRANSFERASE ACTIVITY (75) Inventors: Georgios Tzortzis, Reading (GB); Athanasios K Goulas, Reading (GB); Theodoros Goulas, Reading (GB)

(73) Assignee: Clasado Inc., Panama (PA)

( * ) Notice: Subject to any disclaimer, the term of this patent is extended or adjusted under 35 U.S.C. 154(b) by 371 days.

(21) Appl. No.: 12/223,508

(22) PCT Filed: Jan. 23, 2007

(86) PCT No.: PCT/GB2007/000178
§ 371 (c)(1),
(2), (4) Date: Jul. 30, 2008

(87) PCT Pub. No.: WO2007/088324
PCT Pub. Date: Aug. 9, 2007

(65) Prior Publication Data
US 2009/0110770 A1    Apr. 30, 2009

(30) Foreign Application Priority Data
Jan. 31, 2006    (GB) .................................. 0601901.2

(51) Int. Cl.
C12N 9/26 (2006.01)
C12P 21/04 (2006.01)
C07H 21/04 (2006.01)
(52) U.S. Cl. ...... 435/201; 435/69.1; 435/71.1; 536/23.2
(58) Field of Classification Search ........................ None
See application file for complete search history.

(56) References Cited

U.S. PATENT DOCUMENTS

| | | | |
|---|---|---|---|
| 4,435,389 A | 3/1984 | Mutai et al. | |
| 4,944,952 A | 7/1990 | Kobayashi et al. | |
| 5,149,640 A | 9/1992 | Oonishi et al. | |
| 5,294,546 A | 3/1994 | Dombou et al. | |
| 2002/0086358 A1 | 7/2002 | Jorgensen et al. | |
| 2004/0131659 A1 | 7/2004 | Gibson et al. | |

FOREIGN PATENT DOCUMENTS

| | | |
|---|---|---|
| EP | 0 262 858 A2 | 4/1988 |
| EP | 0 438 182 A1 | 7/1991 |
| EP | 1 227 152 A1 | 7/2002 |
| GB | 2 412 380 B | 11/2005 |
| JP | 62059290 | 3/1987 |
| JP | 3049692 | 3/1991 |
| JP | 3049693 | 3/1991 |
| JP | 3246296 | 11/1991 |
| JP | 5-146273 | 6/1993 |
| JP | 05-146296 | 6/1993 |
| JP | 7089976 | 4/1995 |
| JP | 9121853 | 5/1997 |
| JP | 10023898 | 1/1998 |
| WO | WO 88/08025 | 10/1988 |
| WO | WO 96/06924 | 3/1996 |
| WO | WO 00/33854 A | 6/2000 |
| WO | WO 00/46345 | 8/2000 |
| WO | WO 01/90317 A2 | 11/2001 |
| WO | WO 2004/074496 A1 | 9/2004 |
| WO | WO 2005/003329 A1 | 1/2005 |
| WO | WO 2007/054459 A2 | 5/2007 |

OTHER PUBLICATIONS

Branden et al. Introduction to Protein Structure, Garland Publishing Inc., New York, p. 247, 1991.*
Poulsen et al. Q9F4D6—UniProt Databases. Mar. 2001.*
International Search Report, dated May 14, 2007, corresponding to PCT/GB2007/000178.
Written Opinion of the International Searching Authority, dated May 14, 2007, corresponding to PCT/GB2007/000178.
Database EMBL (Online) Oct. 26, 2000, "*Bifidobacterium bifidum* gene for beta-galactosidase (3701 bp)" 3 pages, XP002429539.
Database UniProt (Online) Mar. 1, 2001, "Beta-galactosidase (EC 3.2.1.23)." 1 page XP002429540.
Lawson, Paul A., et al., "Recognition of *Fusobacterium nucleatum* subgroups Fn-1, Fn-2 and Fn-3 by ribosomal RNA gene restriction patterns"; FEMS Microbiology Letters 65 (1989), pp. 41-46.
Krieg, P.A., et al.; "In Vitro RNA Synthesis with SP6 RNA Polymerase", Methods in Enzymology, 1987, vol. 155, pp. 397-415.
Karlsson, Karl-Anders, et al., "Animal Glycosphingolipids as Membrane Attachment Sites for Bacteria", Annu. Rev. Biochem. 1989, 58:309-50.
Møller, Peter L., et al., "Intra- and Extracellular β-Galactosidases from *Bifidobacterium bifidum* and *B. infantis*: Molecular Cloning, Heterologous Expression, and Comparative Characterization", Applied and Environmental Microbiology, May 2001, pp. 2276-2283.
Dumortier, Vincent, et al., "Primary structure of ten galactosides formed by transglycosylation during lactose hydrolysis by *Bifidobacterium bifidum*"; XP-002307221; 1990 Elsevier Science Publishers B.V., Carbohydrate Research, 201 (1990) pp. 115-123.
Paton, James C., et al., "Pathogenesis and Diagnosis of Shiga Toxin-Producing *Escherichia coli* Infections", Clinical Microbiology Reviews, Jul. 1998, pp. 450-479.
Albersheim, et al., "*A Method for the Analysis of Sugars in Plant Cell-Wall Polysaccharides by Gas-Liquid Chromatography*", Carbohydrate Research, 5, 1967, pp. 340-345.
Blakeney, A.,et al., "*A Simple and Rapid Preparation of Alditol Acetates for Monosaccharide Analysis*", Carbohydrate Research, Elsevier Scientific Publishing Co., vol. 113 (1983) pp. 291-299.
Blanchette, D., et al., "α- and β-*Galactosidase properites of Bifidobacterium infantis*", Milchwissenschaft, vol. 47, No. 1, (1992), pp. 18-21.
Bouquelet, S. et al., "*Primary Structure of Ten Galactosides formed by Transglycosylation During Lactose Hydrolysis by Bifidobacterium Bifidum*", Carbohydrate Research, vol. 201, 1990 pp. 115-123.

(Continued)

*Primary Examiner* — Yong Pak
(74) *Attorney, Agent, or Firm* — Christie, Parker & Hale, LLP (57) ABSTRACT

The present invention concerns a β-galactosidase with transgalactosylating activity isolated from *Bifidobacterium bifidum*. The β-galactosidase is capable of converting lactose to a mixture of oligosaccharides which are β-linked and unexpectedly produces the α-linked disaccharide galactobiose. The mixture may be incorporated into numerous food products or animal feeds for improving gut health by promoting the growth of bifidobacteria in the gut, and repressing the growth of the pathogenic microflora.

3 Claims, 6 Drawing Sheets

OTHER PUBLICATIONS

Carpita, N., et al., "*Linkage Structure of Carbohydrates by Gas Chromatography-Mass Spectrometry (GC-MS) of Partially Methylated Alditol Acetates*", Analysis of Carbohydrates by GLC and MS, pp. 157-216, 1989.

Chabaud, et al., "*Contribution of Interleukin 17 to Synovium Matrix Destruction in Rheumatoid Arthritis*", Cytokine, vol. 12, No. 7, Jul. 2000, pp. 1092-1099.

Ciucanu, I., et al., "*A Simple and Rapid Method for the Permethylation of Carbohydrates*", Carbohydrate Research, 131 (1984) pp. 209-217, Elsevier Science Publishers.

Crittenden; R., "*Prebiotics*"; Probiotics: A Critical Review ISBN 1-898486-15-8; 1999 Horizon Scientific Press, Wymondham, U.K., pp. 141-156.

Database UniProt [Online] Nov. 1, 1999, "*Alpha-galactosidase (EC 3.2.1.22).*" XP002431984 retrieved from EBI accession No. UNIPROT:Q9XCX2; Database accession No. Q9XCX2, see sequence.

Database Geneseq [Online] Nov. 19, 2002, "*Bifidobacterium longum NCC2705 ORF amino acid sequence SEQ ID No. 919.*" XP002431983 retrieved from EBI accession No. GSP:ABP66175; Database accession No. ABP66175; see SEQ ID No. 919.

Database UniProt [Online] Sep. 27, 2005, "*Glycoside hydrolase, clan GH-D.*" XP002431985 retrieved from EBI accession No. UNIPROT:Q40Z83; Database accession No. Q40Z83, see sequence.

Database UniProt [Online] Dec. 20, 2005, "*Alpha-galactosidase (EC 3.2.1.22).*" XP002431987 retrieved from EBI accession No. UNIPROT:Q2XQ11; Database accession No. Q2XQ I I, see sequence.

Database UniProt [Online] May 30, 2006, "*Alpha-galactosidase (EC 3.2.1.22).*" XP002431986 retrieved from EBI accession No. UNIPROT:Q1KTD9; Database accession No. Q1KTD9, see sequence.

Doares, Steven, et al., "*An Improved Method for the Preparation of Standards for Glycosyl-linkage Analysis of Complex Carbohydrates*", Carbohydrate Research, 210 (1991) pp. 311-317, Elsevier Science Publishers.

Dumortier, V., et al; "*Purification and properties of a β-D-galactosidase from Bifidobacterium bifidum exhibiting a transgalactosylation reaction*"; Biotechnol. Appl. Biochem. 19, pp. 341-354 (1994).

Gibson, G., et al., "*Dietary Modulation of the Human Colonic Microbiota: Introducing the Concept of Prebiotics*", Critical Review, American Institute of Nutrition, 1995, pp. 1401-1412.

Gibson; G. "*Bifidobacteria and Oligosaccharides-The Functional Use of Prebiotics*"; Positive Nutrition: Functional Foods; IBC Technical Services, London 1995, 34 pages.

Gibson; G., "*Prebiotics: New Developments in Functional Foods*"; Chandos Publishing, Oxford 2000, 96 pages.

Gopal, P.K., et al., "*Utilisation of galacto-oligosaccharides as selective substrates for growth by lactic acid bacteria including Bifidobacterium lactis DR 10 and Lactobacillus rhamnosus DR20,*" International Dairy Journal 11 (2001) pp. 19-25.

Goulas A et al: "*Development of a process for the production and purification of α- and β-galactooligosaccharides from Bifidobacterium bifidum NCIMB 41171*" International Dairy Journal, vol. 17, No. 6, Jun. 2007, pp. 648-656, XP002431977.

Hanatani, Mitsuya et al., "*Physical and Genetic Characterization of the Melibiose Operon and Identification of the Gene Products in Escherichia coli*"; The Journal of Biological Chemistry, Feb. 10, 1984, vol. 259, No. 3, pp. 1807-1812.

Hashimoto, H., et al., "*Production of the Positional Isomers of α-Galactobiose by the Reverse Reaction of α-Galactosidase Candida guilliermondii H-404*" , Journal of Applied Glycoscience, vol. 48, No. 3, (2001), pp. 279-285.

Hashimoto, H., et al., "*Candida guilliermondii H-404*", Journal of Applied Glycoscience, vol. 41, No. 2, (1994), pp. 143-150 (includes English abstract).

Hung et al., "*Molecular and Biochamical Analysis of Two Beta-Galactosidases from Bifidobacterium Infantis, HL96, Appln Environ Microbiol.* 67(9)"4256-63, 2001.

Ito, et al.; "*Effects of Administration of Galactooligosaccharides on the Human Faecal Microflora, Stool Weight and Abdominal Sensation*"; Microbial Ecology in Health and Disease, vol. 3:285-292 (1990).

Ito, et al.; "*Effects of Transgalactosylated Disaccharides on the Human Intestinal Microflora and Their Metabolism*"; J. Nutr. Sci. Vitaminol., 39, 279-288, 1993.

Lamoureux L et al: "*Production of Oligosaccharides in Yogurt Containing Bifidobacteria and Yogurt Cultures*" Journal of Dairy Science, American Dairy Science Association, Savoy, IL, US, vol. 85, No. 5, May 2002, pp. 1058-1069, XP001124200; ISSN: 0022-0302 the whole document, in particular Table 5.

MacCormick, C.A., et al., "*Characterization of a Variant of the Polysaccharide Acetan Produced by a Mutant of Acetobacter Xylinum Strain CR1/4*", Journal of AppliedBacteriology 1993, 74, pp. 196-199.

MacFarlane, G., et al., "*Validation of a Three-Stage Compound Continuous Culture System for Investigating the Effect of Retention Time on the Ecology and Metabolism of Bacteria in the Human Colon*", Microbial Ecology, 1998, 35:180-187.

Matsumoto et al., "*Galactooligosaccharides*", Japanese Technology Reviews, Section E, Chapter 5, vol. 2.3, 1993, pp. 90-94 (9 sheets).

Olano-Martin, E., et al; "*Pectins and Pectic-oligosaccharides inhibit Escherichia coli O157:H7 Shiga toxin as directed towards the human colonic cell line HT29*"; FEMS Microbiology Letters 218 (2003), pp. 101-105.

Onishi, N., et al; "*Production of Galacto-Oligosaccharide from Lactose by Sterigmatomyces elviae CBS8119*", Applied and Environmental Microbiology, Nov. 1995, pp. 4022-4025.

Palframan, et al., "*Carbohydrate Preferences of Bifidobacterium Species Isolated from the Human Gut*", Current Issues in Intestinal Microbiology, vol. 4, 2003, pp. 71-75.

Prenosil, J.E., et al; "*Formation of Oligosaccharides during Enzymatic Lactose: Part 1: State of Art*"; Biotechnology and Bioengineering, vol. 30, pp. 1019-1025 (1987).

Rabiu, B., et al; "*Synthesis and Fermentation Properties and Novel Galacto-Oligosaccharides by β-Galactosidases from Bifidobacterium Species*"; Applied and Environmental Microbiology, Jun. 2001, pp. 2526-2530.

Rowland et al., "*The effects of transgalactosylated oligosaccharides on gut flora metabolism in rats associated with a human faecal microflora*", Journal of Applied Bacteriology, 1993, 74, pp. 667-674.

Russel P., 2002 iGenetics, Pearson Education, Inc., San Francisco, pp. 187-189.

Sako, T., et al; "*Recent progress on research and applications of non-digestible galacto-oligosaccharides*"; International Dairy Journal 9 (1999), pp. 69-80.

Sambrook, J. et al., Molecular Cloning: A Laboratory Manual, vol. 3, Third Edition, (2002), Chapter 15, "*Expression of Cloned Genes in Escherichia coli,*" pp. 15.1-15.65 www.MolecularCloning.com.

Scalabrini P et al:, "*Characterization of Bifidobacterium Strains for Use in Soymilk Fermentation*" International Journal of Food Microbiology, Elsevier Science Publishers, Amsterdam, NL, vol. 39, No. 3, 1998, pp. 213-219, XP000952364, ISSN: 0168-1605 the whole document, in particular Table 1.

Schell, et al., "*The genome sequence of Bifidobacterium longum reflects its adaptation to the human gastrointestinal tract*", Proceedings of the National Academy of Science, vol. 99, Oct. 29, 2009, pp. 14422-14427 (including PNAS Corrections, Jun. 28, 2005, pp. 9429-9430).

Smeianov et al., GenBAnk accession No. AAG02023, 2000.

Sweet, David, et al., "*Quantitative Analysis by Various G.L.C. Response-Factor Theories for Partially Methylated and Partially Ethylated Alditol Acetates, Carbohydrate Research*", 40 (1975) pp. 217-225, Elsevier Science Publishers.

Tanaka, R., et al; "*Effects of Administration of TOS and Bifidobacterium breve 4006 on the Human Fecal Flora*"; Bifidobacteria Microflora, vol. 2(1), 17-24, 1983.

Tzortzis, G., et al: "*Synthesis of prebiotic galactooligosaccharides using whole cells of a novel strain, Bifidobacterium bifidum NCIMB 41171*" Applied Microbiology and Biotechnology, Springer-Verlag, BE, vol. 68, No. 3, Aug. 1, 2005, pp. 412-416, XP019331926; ISSN: 1432-0614.

Van Den Broek. L A M, et al: "*Synthesis of alpha-galacto-oligosaccharides by a cloned alpha-galactosidase from Bifidobacterium adolescentis*" Biotechnology Letters, vol. 21, No. 5, May 1999, pp. 441-445, XP009083120; ISSN: 0141-5492 the whole document, in particular p. 443, left-handed column, last paragraph.

Van Laere K, M J, et al: "*Transglycosidase activity of Bifidobacterium adolescentis DSM 20083 alpha-galactosidase*" Applied Microbiology and Biotechnology, Springer Verlag, Berlin, DE, vol. 52, No. 5, Nov. 1999 pp. 681-688, XP002285615; ISSN: 0175-7598 the whole document.

Van Laere, K.,et al; "*Characterization of a Novel β-Galactosidase from Bifidobacterium adolescentis DSM 20083 Active towards Transgalactooligosaccharides*", Applied and Environmental Microbiology, Apr. 2000, pp. 1379-1384.

Yuan, et al., "*Feruloyl oligosaccharides stimulate the growth of Bifidobacterium bifidum*", Anaerobe, vol. 11, 2005, pp. 225-229.

Zarate, S., et al; "*Oligosaccharide Formation During Enzymatic Lactose Hydrolysis: A Literature Review*"; Journal of Food Protection, vol. 53, No. 3, pp. 262-268 (Mar. 1990).

Ziggers, D., "*TOS, a new prebiotic derived from whey*," FEED MIX, vol. 9, No. 6, 2001, pp. 7-9.

International Search Report for PCT/GB2004/002815 dated Jul. 12, 2004.

International Search Report, dated Jul. 4, 2007, corresponding to PCT/GB2007/001081.

Written Opinion of the International Searching Authority, dated Jul. 4, 2007, corresponding to PCT/GB2007/0001081.

International Search Report dated Jun. 11, 2007, corresponding to PCT/GB2006/004796, 5 sheets.

International Preliminary Examination Report, dated Jul. 3, 2008, for International Patent Application No. PCT/GB2006/004796.

International Preliminary Report on Patentability and Written Opinion of the International Searching Authority dated Oct. 9, 2008, for corresponding International application No. PCT/GB2007/001081.

Japanese Office Action dated Dec. 9, 2008, in corresponding Japanese Patent Application No. 2006-500267, along with English translation.

U.S. Office Action dated Sep. 8, 2010 for U.S. Appl. No. 12/225,626.

U.S. Office Action dated Oct. 20, 2010 for U.S. Appl. No. 12/086,834.

U.S. Office Action dated Oct. 6, 2009 for U.S. Appl. No. 10/552,483.

An, et al, "*Isolation of Phaffia rhodozyma Mutants with Increased Astaxanthin Content*", Applied and Environmental Microbiology, vol. 55, No. 1, Jan. 1989, pp. 116-124.

Seffernick, et al., "*Melamine Deaminase and Atrazine Chlorohydrolase: 98 Percent Identical but Functionally Different*", Journal of Baceteriology, vol. 183, No. 8, Apr. 2001, pp. 2405-2410.

Witowski, et al., "*Conversion of a β-Ketoacyl Synthase to a Malonyl Decarboxylase by Replacement of the Active-Site Cysteine with Glutamine*", Biochemistry, vol. 38, No. 36, 1999, pp. 11643-11650.

Database EMBL (Online) "*Bifidobacterium breve B-galactosidase (B-gal) gene, complete cds*", Accession No. AY691690, Aug. 24, 2004 (2 sheets).

International Search Report and Written Opinion dated May 18, 2007 for International Application No. PCT/EP2006/068029 (9 sheets).

International Preliminary Report on Patentability dated May 14, 2008 for International Application No. PCT/EP2006/068029 (7 sheets).

International Search Report and Written Opinion dated Sep. 4, 2009 for International Application No. PCT/GB2009/001302 (9 sheets).

U.S. Notice of Allowance dated Oct. 28, 2010 for U.S. Appl. No. 10/552,483 (12 sheets).

U.S. Office Action dated Feb. 15, 2011 for U.S. Appl. No. 12/084,681 (27 sheets).

U.S. Notice of Allowance dated Feb. 24, 2011 for U.S. Appl. No. 12/086,834 (5 sheets).

\* cited by examiner

Figure 1

```
   1 ggatccggtg aacgcgccga gcgcggtgta cgtgctgcgc tcgtgcgagt cggaggagat
  61 cgcggggatc atgccccagt aggagatgtc gcgcagcgag tagatcacgt cgagcaggat
 121 gaacacgatg acgaacagga ccatgaacac gccggtgttc acatccacga ggccgaacag
 181 gccggtgaac accatgatca gcaggatgcc aggcacgatg ccgccaatga actgccacgg
 241 gcggaaccgg ccccagcggg tgttcgtgtt gtccacgagg ttgccgagca gcgggtcgag
 301 aaagatctcc gcgatgcgga tgaccaccac gagtccggtg atcaccgcga tgaggcgttt
 361 ggcaagcgtc ttgtccacgt cgatgaacag cgcggtggtc acgaacgtga tgaagaacgt
 421 gctcattgtg ttgtagaacg cggcctggcc caggttaccg aatgcgtatg cgatcttctg
 481 acccgtgttc cgcgtgggct gcggccttcc ggtcgtttcc gtgtgttgtg tggtggatcc
 541 gctcatggtg tggtggcctc cttgcgacct gtaaagaatc cgtgcgcgtg aaccgctccg
 601 atcccgcaaa gcgtgagtat agaactttct tgaaaaagta gaaaactata ccgcgtgtcg
 661 caaatcatgc caacgttctg caaccggcac tccgtgtgga tgagtaaggt ttgaagcctg
 721 cttgatgtgc ttgaatctta agaaatccac gtattctgca tgttgcaggc cttgtgccgc
 781 gaaatgctgg aaagaatttg cgcaatcaag taacaatatt tatccttgtt gtacaaggaa
 841 cccgattcaa cgaggttccc tcactgcggc ggcaacgacg cgacgcaatc cgatgcgaaa
 901 gcgaggacat catgaacaca accgacgatc agcggaagaa cggcgatccg atcgtctccc
 961 cgtccatacc gacgacggca tggctcgccc acccgcgcgt gtacgcggtt caccggctcg
1021 acgcccattc cgatcatgcg tgctggtctc gctccccagt cgacggcgag agcacgaatc
1081 tcaggcagag ccttgacggc gaatggcggg tccgcgtcga gacggcgccg acgggccgtt
1141 tccccgatgg gacgagcgac gggccggact ggatcagcga cgtgtcgcct ctgttcgccg
1201 cgcccggatt cgacgattcg tcgttctcac gcgtgcaggt gccctcgcat ctggagactg
1261 cggggctgct tgccccgcag tacgtgaacg tgcagtaccc atgggacgga catgaggacc
1321 cgaaggcccc ggccatcccc gagcatggcc atgtggcggt ctaccggcgc gagttcgacg
1381 cggatggcga agtcgcccag gccgtgcgcg aagggcgccc ggtgacgctt accttccagg
1441 gcgcggccac agccatctac gtgtggctca acggctcgtt cgttggctac gccgaggact
1501 ccttcacgcc cagcgagttc gacgtgacgg acgcgatcaa ggtggacggc aacgtgctgg
1561 cggtcgtctg ctacgagtat tcgagcgcga gctggttgga ggatcaggac ttctggcgtc
1621 tgcacggcct gttccgctcc gtcgaactca acgcgaggcc cgccgcccac atcgccgacc
1681 tccatgccga cgccgactgg gatctcgcca catcaagggg ttcgctctcg ctggatgtgc
1741 tgatcgacgg tgccgcgaac gccgcgacgg tcgacttcgc actgtgggac aagaacggca
1801 ccatcgtctg gcacaccgcc acgaaagcgg acggaacgct gcacgccgag gccgagatcg
1861 atgacgcggc gccatggagc gccgaacgcc ccgacctgta cgagctatcc gtcaccctgc
1921 tcgacgcgga cggcaaggtc ctggagaccg ctcgcactcg atcggcttc cggcatgtgg
1981 ccatcgagga cggcatcctc aagctcaacg gcaagcgcct cgtgttccgt ggcgtcaacc
2041 gccacgagtt cgactgccgg cgcggccggg ccatcaccga agaggacatg ctgtgggaca
2101 tccgcttcat gaagcgccac aacatcaacg cggtgcgcac ctcgcactat ccgaaccagt
2161 cgcgctggta cgagctgtgc gacgaatacg gcatctacct gatcgacgag accaatctgg
2221 agacccatgg cagctggaac agccccggcg acatccccgt gggaacctcc gtccccggtg
2281 acgacgaggc ctggctgggc gcgtgcatcg accggctgga cagcatgatc ctgcgcgacc
2341 gcaaccatcc cagcgtgctc gtctggtcgc tgggcaacga atcctacgcg ggcgaagtcc
2401 tcaaggccat gagcgcgcac gcgcaccggc ttgatccggg tcgtcccgtc cactacgaag
2461 gtgtcaactg gaaccatgcc tacgacggga tcagcgactt cgaaagccgt atgtacgcca
2521 agccggccga gatccaagac tggctcgaac acggcgacga acggggcgag gcgagcaagc
2581 cgttcgtcag ctgtgagtac atgcatgcca tgggcaactc gtgcggcggt ctgagcgagt
2641 tcatcgacct cgaacggtac gagcgctact ccggcgggtt catctgggat tacatcgacc
2701 aggggctcgt ccagcgtctg cccgacggga gcgaacgcct cagcgtcggc ggagaatggg
```

Figure 1 (continuation)

```
2761 gcgaccgtcc aaccgactac gaattcgtgg gcaacggcat cgtgttcgcc gaccgcacgc
2821 ccagccccaa ggcgcaggag gtcaagcagc tgtattcgcc ggtcaagctc gccccgacg
2881 ggcacggcgt gaccatcgag aaccgcaacc tgttcgccgg caccgacggc tacgtgttcg
2941 ccgcacggct cctcgaagac gggcatgaga tctggcatgc cgactaccgt ttcgacgtgg
3001 ccgcaggaga tacccaacac catgacatcg ccttcccgga catcgacgcg gacggggata
3061 cgcgcgaagt cacctacgag gtcgatctcc tgctcgccga agccaccgca tgggcgccgg
3121 ccggctacga gctcgcgttc ggccaactca ccggcacgct caaccccgaa caggacatca
3181 ccgagaccag ccatgacgac gacggccgcg caactcgcac gctcagccga tggaacgccg
3241 gcatccgccg cgacgacgag gaaattctcc tgtcacgcac tcagggaggc atcgtctcct
3301 ggaagcgcga cgaccgggaa atggtcatcc gtcgccccga actcgtcacg ttccgcccat
3361 tgaccgacaa cgatcgcggt aaccattccg gtttcgaccg tgccgcatgg ttcgcggccg
3421 gccgatacgc catcgtaacc gaaacgaaaa tccatgaaag cgatgacggt ctcgtagcgg
3481 aataccagta cgaacttgcc gatccgaacc acacgcccgt gtccgtcact taccatgtca
3541 actccgatat gcgtatgcaa ctgaccgtcg aatacccggg gaacgccact gacatggcca
3601 gtctgcccgc gttcggtatc gaatgggagc tgcccggcga atacgatcgt ctgcgctact
3661 acggccccgg ccccgaggag acctaccgcg accgtaagca gggcggcaag ctcggcatct
3721 gggacgccac cgcgaaggcg agcatggcgc cgtatctcat ggtgcaggaa accggcagcc
3781 acgaggacgt ccgctggctc gaagccaccg acatccaagg ccacggattg cgcgtcaccc
3841 aacgcggcga ccgtcacttc acggccagcc tgctgccctg gaacacctac acgatcgagg
3901 ccgcgcgccg ccacgaggac ctgcccaaac cgcgccacaa ctacctgcgc ctgctcgcgg
3961 cccagatggg cgtcggtgga gacgactcct ggggagcccc cgtccacacg gcctaccagc
4021 tgcccgccgg caggccgctc accctcgacg tgaacctcga actcatctga ccggcaacgg
4081 gcggcggcat gcaccaccat gccgccgccg gccccgccta cgacgcggcg atcgaggcca
4141 cgggcgctgc ggccgcggac ggcaccggcg aggaggcgtt cgagcgcgcc ggccacgcgg
4201 tccacggcac caccgccag gtcctctcgc tcatcaccaa cccgatggac gtgatctgcc
4261 gcaacatccg caccgtgcgc gagaagatgg caacccgccc cgacatcctc ggctgccacc
4321 tcgaaggccc gttcctcgcc ctcaagtgca agggcgcgca cgattcgaac tgcctcaaag
4381 acccgatgcc cgaactcatg gaccgcatgc tcgacgcctc gggcgccgac ctcgccgccg
4441 gcaagctcgg gtgcatccgc cagatcacca tctcgacccc accgactgga ccgcccaaca
4501 cgtctggtgc gccggccgcc aggtggagta aactccttcc agcaaaatcg acgccggtgc
4561 cgcccgtctc gagacgacgt cttacgcctg aggaacgaag cttgcgcgcg gcaccagttc
4621 ggtcgtcagc aggatgtgac gacgcacccg ccgctcatgc ttcaacccat cgatcagggt
4681 ggagaacgcc atgcgggcca actcccttg atcgatcgca tacgaactca gcggcggcga
4741 cgtgtaccgg gcgatcgact ggttgttcac actcaccacg gccaactcgt cgggaacctc
4801 cacgcgcagt gcgttcaacg cctgcaacgc ccccaccgca agcacgtcgg cggccacgat
4861 caaaccatcg ggcatgctgc cggcctcacg atggtcagcc accaactgct ccgcgagacg
4921 atagccgttc tccacggtga acgtgccgga cgaatacacc aatccgtccg tttccaatcc
4981 cagatgcgcg gcccactgac ggaacgacag ctcgcgaatg tcctcgggat agtcatgcat
5041 gcccatgatg ctgcccacgc cgccgagaaa cgcgatatga ctgcggcccg ccgcgatcat
5101 cgcgtccaag gcgtccagca tcgtctgcga cagatcggga cacacggagt cgaacaggcg
5161 cggcgccgga ttcgtgtcga tgcacacgcc atgcgggagc accatatgca gggctcgcag
5221 gtccgcttcg ggaaacaccg tggctcccac ggtgatgaac ccatcaaact ccgttgcgcg
5281 ttccgtcaac tcgtgtatgg acaacgtgag ctggtccaat tccaacgact ccgcacgctc
5341 cgcaagaacc ttccgcagat cggcgaagta cgcgtcctgc aattcctccc cggacggagg
5401 cgcatccaac accgcgatcg cgggacggaa cacgttgcga taccccatct cctcgcacac
5461 gcgcaacaca cgccgacgcg tctcctcctt gatggagaac gacgggtcgt tcaacaagcg
```

Figure 1 (continuation)

```
5521 tgacaccgtg ctctgcgaca ccccggcccg tcccgcgact tccttgagcg tggccatgac
5581 atcctccccg caaactttag taaagggttt tactacagca taacccggga aggcggggtt
5641 agcggcattg gcggcgtgga agtttaccca tgactggtag actgcacatg tcccggcaat
5701 aggggcaatg catagggggg tggcgggcat gtgcagcaac attcccgtca ccttacgatt
5761 cttatagcgt gtcaggtaaa agaattatga ttctcaatcc accttccggc cgcgcctgca
5821 gactcaaatg gccatgatgc atagcgacaa tctctcgcac tatggataaa cccaatccgt
5881 gatgaggtga tgcagatccc acatgcgtat ttatcctatt atcctcccct ctgttaaaag
5941 gtgacaggaa atcatctatc ctcgtatcgg aaagatccat gccggtattg gatatgtcta
6001 tcgcaatgca ggactcgcct tcgtattgcc tgtcgttggc taagtttatc catacatgtg
6061 gttgagccgc acgattatgc tgaatggcat tcgtaataag gtttgcaatc atctgtctaa
6121 ttagcagacc atcggctagg atatatgcat tctccagatt ggtatgtact tgaactctat
6181 ctccgataag ttccatattt tcctgaagaa cattgcgaat gatctcagct acattaactc
6241 ggctaagatc agctcggttt aattgctgaa cttcgacaa ttcgagcaga tgattgacga
6301 tttcaacccc agcatgattt gaagccaaag ccttttcgac gaaaggtctg caacgctcat
6361 cgaaaagctg gttgtgcagc ggaatctcca atgcggccga agtggccgca agtggatttt
6421 ttaactcatg tgacgcatcg gcgataaatt cctttccccg actgattgcg ctgttgagat
6481 cctttaacat gaggttgtat gcggatgcaa tagtgtacgc ctcgtcgttt tcatatggaa
6541 taacgatagg ttgccttttcc aatccagcgt cggacgcgat aatctgagag gccacactat
6601 tgattcttcg ttgtgtccta gtggcgataa tccaagttat tcctccagat aatatgccga
6661 aaacaatgat gggggctatg cttaccgcca atatcagatc ccgggatttt atgtctcctt
6721 gttccatagt tagcgttaaa gcatccttac cggagtcata cccggcagaa acgtaatcct
6781 taccggagtc aggaggaatg gcttgcgaat tcaaactatg ttgttcatcg gcatcttctg
6841 cctgagtaaa agatttattt acggtcactg tttccagttg ccggttcacg acataatatg
6901 tcatggcggt caccactccg gtaagcatga agaacacgat gacgatcgtg gtgaccaatc
6961 ttcttcttgt agaccactga aacggtaaac gcagtttcgg atggctggaa tggctcccat
7021 tcgacgaagg atattcaggc tttttcatga tatgcgatat ccttgtccgg gaacggtttc
7081 aatgaaatca gtgattccga ttttcgtgcg aatcgcatag attgtggtct tgacgattcc
7141 tctcgtatga gcgtgatcat cctgccaaat ctcacgatat agacattccg cactaatcac
7201 cgcacctcgc gcctcaatca gcgtcctcaa tacggcaagt tctcgtttcc caaactttag
7261 ttctgcaccg cgaaccgtga t
```

Figure 2

```
             10         20         30         40         50         60         70         80         90        100
      ....|....|....|....|....|....|....|....|....|....|....|....|....|....|....|....|....|....|....|....|
   1  MNTTDDQRKNGDPIVSPSIPTTAWLADPRVYAVHRLDAHSDHACWSRSPVDGESTNLRQSLDGEWRVRVETAPTGRFPDGTSDGPDWISDVSPLFAAPGF 110        120        130        140        150        160        170        180        190        200
      ....|....|....|....|....|....|....|....|....|....|....|....|....|....|....|....|....|....|....|....|
 101  DDSSFSRVQVPSHLETAGLLAPQYVNVQYPWDGHEDPKAPAIPEHGHVAVYRREFDADGEVAQAVREGRPVTLTFQGAATAIYVWLNGSFVGYAEDSFTP 210        220        230        240        250        260        270        280        290        300
      ....|....|....|....|....|....|....|....|....|....|....|....|....|....|....|....|....|....|....|....|
 201  SEFDVTDAIKVDGNVLAVVCYEYSSASWLEDQDFWRLHGLFRSVELNARPAAHIADLHADADWDLATSRGSLSLDVLIDGAANAATVDFALWDKNGTIVW 310        320        330        340        350        360        370        380        390        400
      ....|....|....|....|....|....|....|....|....|....|....|....|....|....|....|....|....|....|....|....|
 301  HTATKADGTLHAEAEIDDAAPWSAERPDLYELSVTLLDADGKVLETARTRIGFRHVAIEDGILKLNGKRLVFRGVNRHEFDCRRGRAITEEDMLWDIRFM 410        420        430        440        450        460        470        480        490        500
      ....|....|....|....|....|....|....|....|....|....|....|....|....|....|....|....|....|....|....|....|
 401  KRHNINAVRTSHYPNQSRWYELCDEYGIYLIDETNLETHGSWNSPGDIPVGTSVPGDDEAWLGACIDRLDSMILRDRNHPSVLVWSLGNESYAGEVLKAM 510        520        530        540        550        560        570        580        590        600
      ....|....|....|....|....|....|....|....|....|....|....|....|....|....|....|....|....|....|....|....|
 501  SAHAHRLDPGRPVHYEGVNWNHAYDGISDFESRMYAKPAEIQDWLEHGDERGEASKPFVSCEYMHAMGNSCGGLSEFIDLERYERYSGGFIWDYIDQGLV 610        620        630        640        650        660        670        680        690        700
      ....|....|....|....|....|....|....|....|....|....|....|....|....|....|....|....|....|....|....|....|
 601  QRLPDGSERLSVGGEWGDRPTDYEFVGNGIVFADRTPSPKAQEVKQLYSPVKLAPDGHGVTIENRNLFAGTDGYVFAARLLEDGHEIWHADYRFDVAAGD 710        720        730        740        750        760        770        780        790        800
      ....|....|....|....|....|....|....|....|....|....|....|....|....|....|....|....|....|....|....|....|
 701  TQHHDIAFPDIDADGDTREVTYEVDLLLAEATAWAPAGYELAFGQLTGTLNPEQDITETSHDDDGRATRTLSRWNAGIRRDDEEILLSRTQGGIVSWKRD 810        820        830        840        850        860        870        880        890        900
      ....|....|....|....|....|....|....|....|....|....|....|....|....|....|....|....|....|....|....|....|
 801  DREMVIRRPELVTFRPLTDNDRGNHSGFDRAAWFAAGRYAIVTETKIHESDDGLVAEYQYELADPNHTPVSVTYHVNSDMRMQLTVEYPGNATDMASLPA 910        920        930        940        950        960        970        980        990       1000
      ....|....|....|....|....|....|....|....|....|....|....|....|....|....|....|....|....|....|....|....|
 901  FGIEWELPGEYDRLRYYGPGPEETYRDRKQGGKLGIWDATAKASMAPYLMVQETGSHEDVRWLEATDIQGHGLRVTQRGDRHFTASLLPWNTYTIEAARR 1010       1020       1030       1040       1050
      ....|....|....|....|....|....|....|....|....|....|.
1001  HEDLPKPRHNYLRLLAAQMGVGGDDSWGAPVHTAYQLPAGRPLTLDVNLELI
```

GALACTOSIDASE WITH α-GALACTOSYLTRANSFERASE ACTIVITY

CROSS-REFERENCE TO RELATED APPLICATION

This application is a National Phase Patent Application of International Application Number PCT/GB2007/000178, filed on Jan. 23, 2007, which claims priority of British Patent Application Number 0601901.2, filed on Jan. 31, 2006.

PRODUCT AND PROCESS

The present invention relates to a β-galactosidase with transgalactosylating activity capable of converting lactose to a mixture of oligosaccharides which are β-linked and unexpectedly produces the α-linked disaccharide α 1-6 galactobiose. In particular it relates to a β-galactosidase isolated from a recently discovered strain of *Bifidobacterium bifidum*.

The invention particularly relates to DNA sequences encoding the isolated β-galactosidase enzyme, to the enzyme encoded by such a DNA sequence and to a host cell comprising the DNA sequence or a recombinant vector incorporating the DNA sequence. The invention also relates to the use of the enzyme encoded by a DNA sequence, or of the host cell containing a DNA sequence or recombinant vector, to produce oligosaccharides.

Bifidobacteria naturally colonise the lower intestinal tract, an environment which is poor in mono and disaccharides since such sugars are preferentially consumed by the host and microbes present in the upper intestinal tract. In order to survive in the lower intestinal tract bifidobacteria produce various kinds of exo- and endoglycosidases in surface bound and/or extracellular forms, by which they can utilise diverse carbohydrates.

Besides hydrolase activity, some enzymes from bifidobacteria show transferase activity. This transglycosylation activity of glycosidases is extensively used for the enzymatic synthesis of various oligosaccharides, which have proven to act as bifidobacteria growth promoting factors.

It is known that members of bifidobacteria produce β-galactosidase enzymes that are involved in the bacterial metabolism of lactose. Møller, P. L. et al in *Appl & Environ. Microbiol.*, (2001), 62, (5), 2276-2283 describe the isolation and characterisation of three β-galactosidase genes from a strain of *Bifidobacterium bifidum*. They found that all three β-galactosidases were able to catalyse the formation of beta-linked galactooligosaccharides by transgalactosylation.

Dumortier et al in *Carbohydrate Research,* 201, (1990), 115-123 described the formation of beta-linked oligosaccharides by a transgalactosylation reaction during lactose hydrolysis with *Bifidobacterium bifidum* DSM 20456. Their analysis of the structure of the mixture of oligosaccharides produced showed that the linkages were β-(1→3), β-(1→6) and β-(1→4)-D-galactosyl linkages. Dumortier suggested that compounds produced by *Bifidobacterium bifidum* are involved in the adherence of bacteria in the large intestine.

A strain of *Bifidobacterium bifidum* has been found that is capable of producing a galactosidase enzyme activity that converts lactose to a novel mixture of galactooligosaccharides which unexpectedly contains up to 35% of disaccharides including galabiose (Gal (α 1-6)-Gal). This disaccharide is known (see Paton, J C and Paton, A W (1998), *Clin. Microbiol. Revs.*, 11, 450-479; Carlsson, K A (1989), *Ann. Reviews Biochem.*, 58, 309-350) to be an antiadhesive capable of preventing the adhesion of toxins, eg Shiga toxin and pathogens such as *E. coli*, to the wall of the gut.

This strain of *B bifidum* was deposited under accession number NCIMB 41171 at the National Collection of Industrial & Marine Bacteria, Aberdeen, UK on 31 Mar. 2003. It is also described in UK Patent No 2 412 380.

It has now been found that this strain of *B bifidum* produces several β-galactosidases, one of which unexpectedly exhibits α-galactosyltransferase activity. This enzyme produces a number of different oligosaccharides which are β-linked, but it also produces the α-linked disaccharide galabiose.

According to the invention there is provided a DNA sequence which encodes a protein with an amino acid sequence as given in SEQ. ID NO: 2 or hybridises under stringent conditions to the DNA sequence which encodes this protein. The DNA sequence is given in SEQ. ID NO: 1 or may comprise a fragment or degenerative thereof.

The phrase "degenerative" is construed to mean a DNA sequence which is at least 50% homologous to SEQ. ID NO: 1, preferably from 50 to 98% homologous, most preferably from 75 to 95% homologous.

Such a DNA sequence may comprise nucleotide substitutions, additions or deletions which result in less than 60%, preferably less than 45%, more preferably less than 25% change in the amino acid sequence shown in SEQ. ID NO: 2. Nucleotide substitutions may result in conservative amino acid substitutions.

According to a second aspect of the invention there is provided an enzyme encoded by a DNA sequence as defined above. Such an enzyme may comprise the amino acid sequence given in SEQ. ID NO: 2 or a fragment thereof.

According to a third aspect of the invention there is provided a recombinant vector, preferably an expression vector, comprising a DNA sequence as defined above. Such a vector may be incorporated into a host cell such as a bacterial, yeast or fungal cell. Alternatively, the DNA sequence may be incorporated into such a host cell. A suitable host cell may be selected from *Bifidobacterium, Lactococcus, Lactobacillus, Bacillus* for example *Bacillus subtilus* or *Bacillus circulans, Escherichia* and *Aspergillus* for example *Aspergillus niger.*

Using lactose as a substrate, the enzyme encoded by a DNA sequence as defined above produces a mixture of disaccharides comprising Gal (β1-3) Glc, Gal (β1-3) Gal, Gal (β1-6) Gal and Gal (α1-6) Gal. Also present in the mixture of oligosaccharides are trisaccharides Gal (β1-6) Gal (β1-4) Glc, Gal (β 1-3) Gal (β 1-4) Glc, tetrasaccharide Gal (β 1-6) Gal (β 1-6) Gal (β 1-4) Glc and pentasaccharide Gal (β 1-6) Gal (β 1-6) Gal (β 1-6) Gal (β 1-4) Glc.

The enzyme or the host cell as described above may be used to produce a mixture of disaccharides, including Gal (α 1-6) Gal (galabiose) which may form part of a product for improving gut health. Such a product may be selected from the group consisting of dairy products (for example liquid milk, dried milk powder such as whole milk powder, skimmed milk powder, fat filled milk powders, whey powders, baby milks, baby formula, ice cream, yoghurt, cheese, fermented dairy products), beverages such as fruit juice, infant foods, cereals, bread, biscuits, confectionery, cakes, food supplements, dietary supplements, synbiotic comestible products, prebiotic comestible products, animal feeds, poultry feeds or indeed any other food or beverage.

Alternatively, the oligosaccharides so produced may be used for the preparation of a medicament for example in table or capsule form for preventing the adhesion of pathogens or toxins produced by pathogens to the gut wall. The medicament may be administered to a patient, for example following a course of antibiotic treatment, which often alters or even destroys the normal healthy gut flora.

According to yet a further aspect of the invention there is provided a process for producing an enzyme as defined above which comprises culturing a host cell as defined above in a suitable culture medium under conditions permitting expression of the enzyme and recovering the resulting enzyme from the culture.

The invention is also directed to a process for producing a mixture of oligosaccharides, including the disaccharide Gal (α 1-6)-Gal (galabiose), which comprises contacting the enzyme as defined above or a host cell as defined above with a lactose-containing material under conditions that lead to the formation of the oligosaccharide mixture.

Suitable lactose containing material may be selected from commercially available lactose, whole milk, semi-skimmed milk, skimmed milk, whey and fat-filled milk, whey permeate. Such milk products may be obtained from cows, buffaloes, sheep or goats. Fat-filled milk is defined as whole milk that has been skimmed to remove the dairy fat, which is subsequently replaced by the addition of vegetable fat or oil.

BRIEF DESCRIPTION OF THE DRAWINGS

FIG. 1 shows the nucleotide sequence (SEQ. ID NO: 1) of Bifidobacterium bifidum β-galactosidase of the invention; and FIG. 2 shows the amino acid sequence (SEQ. ID NO: 2) corresponding to the nucleotide sequence of FIG. 1.

Genomic DNA was isolated from the Bifidobacterium bifidum strain (NCIMB 41171) using the method of Lawson et al. (1989) Fems Microbiol Letters, 65, (1-2), 41-45. The DNA was digested with restriction enzymes and fragments having a maximum size of 15 kbp were ligated with pSP72 vector which had been digested with the same restriction enzymes. E. coli cells were transformed with a vector containing insertions consisting of PstI, Eco RI, Bam HI, KpnI, SmaI or HindIII digested chromosomal DNA from the B. bifidum. Clones with β-galactosidase activity were selected on Luria Bertani agar plates containing p-nitrophenyl, X-β-Gal (5-bromo-4-chloro-3-indolyl-β-D-galactoside) and isopropyl-β-D-thiogalactoside (IPTG). Ligation mixtures with Bam HI chromosomal DNA gave rise to seven β-galactosidase positive clones, one of which is identified as pB1.

DNA sequencing of the inserted DNA fragment B1 was performed using the dideoxy chain-termination method of Sanger (Russel P., 2002 iGenetics, Pearson Education, Inc., San Francisco, 187-189) using the BigDye Terminator V.3.O cycle sequencing kit (Applied Biosystems, USA). The DNA sequence of B1 is shown in FIG. 1 (SEQ. ID NO: 1).

The open reading frame (ORF) was located by using the ORF finder from NCBI (National Center of Biotechnology Information). The nucleotide sequence of FIG. 1 was translated in all six possible reading frames and one open reading frame of 1052 amino acids encoding a putative β-galactosidase was identified. The translation is shown in FIG. 2 (SEQ. ID NO: 2).

The present invention will be further described by way of reference to the following example.

EXAMPLE 1

Materials and Methods

All chemicals and media preparations used throughout this study were obtained from Sigma (Dorset, UK), Invitrogen (Paisley, UK), Oxoid (Basingstoke, UK), Qiagen (West Sussex, UK) and Promega (Southampton, UK).

Bacterial Strains

The Bifidobacterium bifidum strain (NCIMB 41171) was maintained on cryogenic beads in Microbank tubes at −70° C. For later experiments, the strain was revived on Wilkinson Chalgren (WC) agar (Oxoid, UK) and TPY medium (trypticase phytone yeast extract medium) and grown anaerobically ($CO_2$ and $N_2$ composition 80% and 20% respectively) at 37° C. for 48 hours. The colony morphology and the absence of contamination were tested by gram staining.

E. coli Strains

Escherichia coli strain DH5a used in this study was commonly incubated under aerobic conditions at 37° C. in Luria Bertani (LB) agar or broth (Sambrook J. and Russell W. D. (2001). Molecular Cloning: A Laboratory Manual. Cold Spring Harbor Laboratory Press, New York) and when necessary was supplemented with antibiotics (100 μg/ml ampicillin and/or 15 μg/ml chloramphenicol) and 40 μl of 2% X-β-Gal, 7 μl of 20% (isopropyl-β-D-thiogalactoside) IPTG which were applied on the surface of a pre-made 90 mm agar plate.

E. coli DH5a strain (Invitrogen, Paisley, UK) (genotype: F⁻ φ80lacZΔM Δ(lacZYA-argF)U169 recA1 endA1 hsdR17($r_k^-$, $m_k^-$) phoA supE44 thi-1 gyrA96 relA1λ⁻) is an α-galactosidase positive strain and was used in expression experiments and for other genetic manipulations.

Genomic DNA Extraction from Bifidobacterium bifidum

Genomic DNA was isolated from the Bifidobacterium bifidum strain (NCIMB 41171) using the following method in which chromosomal DNA was prepared from cell pellet harvested from 100 ml of WC anaerobe broth. The cells were resuspended in 10 ml TES buffer (10 mM Tris-HCl, 10 mM EDTA, 10 mM NaCl, pH 8) and treated with 200 μl of lysozyme/mutanolysin mixture (4:1, lysozyme 10 mg/ml mutanolysin 1 mg/ml) for 30 minutes at 37° C. The cells were then treated with 200 μl of proteinase K (at 20 mg/ml) and 200 μl of RNase (both 10 mg/ml) mixed and incubated for one hour at 65° C. Finally the cells were treated with 2 ml of 10% SDS and incubated for 15 minutes at 65° C. 12 ml of phenol/chloroform were added and the extraction was repeated until the water phase could easily be separated from the interphase. The genomic DNA was precipitated with isopropanol and resuspended in 10 mM Tris-HCl—1 mM EDTA (pH 8). The genomic DNA was then digested with restriction enzymes, ligated into pSP72 digested with the same enzymes and treated with alkaline phosphatase. Digestion of B. bifidum genomic DNA was performed using EcoRI, PstI, BamHI, SmaI and KpnI. Ligation mixtures were used to transform E. coli DH5a and β-galactosidase positive clones were identified as blue colonies on X-Gal-containing plates.

Vector DNA Preparation

The vector used for cloning and expression throughout this study was the pSP72 (Promega, UK) (Krieg, P. A. and Melton, D. A. (1987). In vitro RNA synthesis with SP6 RNA polymerase. Methods in Enzymology. 155: 397-415).

This vector was chosen because of the lack of complementing activity of the α-fragment of β-galactosidase which is not encoded in pSP72. This vector does not carry the short segment of *E. coli* DNA containing the regulatory sequence and the coding information for the first 146 amino acids of β-galactosidase which in combination with *E. coli* strains (ie DH5a) which express the carboxy-terminal portion of this β-galactosidase is giving an active β-galactosidase (α-complementation).

The vector was digested with the following restriction enzymes: PstI, BamHI, HindIII, SmaI, KpnI and EcoRI according to the manufacturer's instructions using a tenfold excess of enzyme over DNA (enzyme units: μgr DNA equal to ten units of enzyme per one μgr of plasmid DNA or ten enzyme units per 0.5 pmol of plasmid DNA). After enzyme heat inactivation (20 min at 65° C.) the restriction patterns were analysed by horizontal gel electrophoresis analysis. The presence of a single fragment in the gel indicated the complete vector digestion and the single restriction digestion of it.

The sufficient digestion of the vector was tested also by transforming unligated molecules into competent *E. coli* DH5a cells. The number of formed colonies on LB agar plates supplemented with ampicillin (100 μgr/ml) was an indicator of the undigested molecules and the expected background during the subsequent experiments.

The vectors were further dephosphorylated with calf intestinal alkaline phosphatase CIAP (Promega, Southampton, UK) according to the manufacturer's instructions. The efficiency of the treatment was tested by self ligation (with Bacteriophage T4 DNA ligase according to manufacturer instructions) following transformation into DH5a cells. The number of formed colonies showed the number of recirculised molecules (non cloned vector) and a subtraction of the above with the formed colonies without CIAP vector treatment shown the number of non dephosphorylated vectors.

Genomic DNA Library Construction

Genomic DNA was partially digested with six restriction enzymes that recognise frequently occurring hexa-nucleotide sequences within prokaryotic DNA. EcoRI, BamHI, PstI, KpnI, SmaI and HindIII are type II restriction endonucleases specifically recognizing the sequences 5'G/AATTC'3, 5'G/GATCC'3, 5'CTGCA/G'3, 5'GGTAC/C3', 5'CCC/GGG3' and 5'A/AGCTT3' respectively, and make double-strand breaks within these sequences generating 5' overhangs of four nucleotides, AATT, GATC, AGCT for EcoRI, BamHI and Hind III respectively, and 3' overhangs, ACGT,GTAC for PstI and KpnI respectively and blunt ends for SmaI.

All these enzymes were active and able to cleave DNA only in the presence of divalent magnesium ions. These ions were the only required cofactor.

Restriction Digestion of DNA

All restriction digestions of the genomic DNA samples were incubated for 2 hours at 37° C. and finally heat inactivated at 65° C. for 20 minutes. The reactions were then cooled at room temperature and the appropriate amount of loading buffer was added, followed by gentle mixing with a sealed glass capillary. The solutions then were loaded into wells of a 0.8% agarose gel (power supply 4-5 volts/cm for 14-16 hours) and the size of the digested DNA was estimated with that of 1 kbp DNA standards (Promega, UK) (Sambrook J. Molecular Cloning: A Laboratory Manual (2002)).

Purification of the Fragments Generated After Restriction Digestion

Fragment purification from the reaction mixtures and the agarose gels was done by using the QIAEX gel extraction kit from Qiagen (West Sussex, UK). Protocols are described with details in the manufacturer's manual.

DNA Ligation and Transformation

After purification of the DNA fragments with the Qiaex gel extraction kit, they were ligated with CIAP-treated pSP72 vector. For ligation, appropriate amounts of DNA were transferred to sterile 0.5 ml microfuge tubes as shown in Table 1.

TABLE 1

Ligation mixtures. Tube A shows the number of self-ligated vector DNA which must be subtracted from the total number of transformants after transformation. Tube B shows the ligation of the vector with the DNA fragments and tube C shows the control in order that the transformation efficiency to be calculated.

| Tube | DNA |
|------|-----|
| A | Vector (15 fmoles [~29.7 ng]) |
| B | Vector (15 fmoles ~29.7 ng DNA) plus insert (foreign 15 fmoles ~69.3 ng) |
| C | pUC control (0.056 fmoles [~100 pg]) |

The molar ratio of plasmid DNA vector to insert DNA fragment should be ~1:1 in the ligation reaction. The final DNA concentration should be ~10 ng/μl.

Before each ligation the DNA fragments were warmed at 45° C. for 5 minutes to melt any cohesive termini that reannealed during fragment preparation. A molar ratio of vector:insert DNA of 1:1 was chosen for all ligation reactions and the reaction assembly was done according to Promega's instructions.

To tubes A and B 1.0 μl of 10× ligation buffer and 0.5 Weiss units of T4 DNA ligase (Promega, UK) were added and the ligation volume was adjusted to 10 μl with molecular biology grade water. To tubes C 1.0 μl of 10× ligation buffer were added and the ligation volume was adjusted to 10 μl with molecular biology grade water.

DNA fragments were added to the tubes together with the water and then warmed to 45° C. for 5 minutes to melt any cohesive termini that were reannealed during preparation. The DNA was chilled to 0° C. before the remainder of the ligation reagents were added and the reaction mixtures were incubated overnight at 16° C. (Sambrook and Russell, 2001).

After ethanol precipitation and purification of the ligated fragments (in order to remove the ligation mixture which cause reduction of the transformation efficiency) transformations were performed according to Hanahan instructions. ~50 ng of ligated DNA in 5μl solution was added to 100 μl of competent *E. Coli* DH5a cells. After heat treatment and expression of the ampicillin resistance gene the cells were spreaded over the surface of LB plates containing ampicillin (100 μgr/ml), X-β-Gal (40 μl of 2% X-β-Gal) and IPTG (7 μl of 20% IPTG).

The number of transformants from each ligation reaction was measured. The number of transformants commonly obtained from tube C was $2 \times 10^5$-$1 \times 10^6$ cfu/μg whereas from tube A was 500-600 cfu/μg. The number of transformants in tube A was an indication of the efficient treatment of the vector DNA. The number of transformants in tube B was in a range from $2$-$4 \times 10^4$ cfu/μg.

Number of Transformants

Ligation mixtures with PstI chromosomal DNA gave rise to 13 β-galactosidase positive clones out of ~2500 screened transformants whereas with BamHI gave rise to 7 positive clones (~1500 scr. transformants), EcoRI gave rise to 3 positive clones (~1300 scr. transformants), KpnI gave rise to 7 positive clones (~2000 scr. transformants), SmaI gave rise to 3 positive clones (~1600 scr. transformants) and HindIII gave rise to 2 positive clones (~1200 scr. transformants).

Positive Clone Digestion

In order to identify the different β-galactosidase genes, the plasmids isolated from the positive clones were digested according to the following table.

|  | Samples | Enzymes |
|---|---|---|
| 1st Digestion | pB1, pB2, pB3, pB4, pB5, pB6, pB7 | BamHI |
| 2nd Digestion | pP1, pP2, pP3, pP4, pP5, pP6, pP7, pP8, pP9, pP10, pP11 | PstI |
| 3rd Digestion | pP12, pP13, pP14 | PstI |
| 4th Digestion | pE1, pE2, pE3 | EcoRI |
| 5th Digestion | pP1, pP12, pB1, pP2, pE1, pE2, pE3 . . . | PstI and EcoRI |
| 6th Digestion | pS1, pS2, pS3 | SmaI |
| 7th Digestion | pP1, pP12, pB1, pP2, pS1, pS2, pS3 | PstI and SmaI |
| 8th Digestion | pK1, pK2, pK3, pK4, pK5, pK6, pK7 | KpnI |
| 9th Digestion | pP1, pP12, pB1, pP2, pK1, pK2, pK3, pK4, pK5, pK6, pK7 | PstI and KpnI |

The first letter (p) indicates plasmid and the insert gene whereas the second letter (P, B, E, S, K) indicates the restriction enzyme that was used for isolation of the respective clone from the genomic DNA.

Gel electrophoresis analysis of the generated fragments after digestion was shown that plasmids pB1, pP1, pP2 and pP11 each have an insert which encodes a different β-galactosidase. The clones containing pB1 was used for further analysis.

DNA Sequencing

DNA sequencing was performed with the dideoxy chain-termination method of Sanger by using the BigDye Terminator v.3.0 cycle sequencing kit (Applied Biosystems, USA) and analysed with the ABI Prism 3100, a fluorescence-based DNA analysis system incorporating capillary electrophoresis.

The 5'- and 3'-ends of the inserted DNA fragments were sequenced with vector specific primers. The inserts were further sequenced by using the Genome Priming System (GPS-1) (New England Biolabs, UK). GPS-1 is a TN7 transposon-based in vitro system which uses TnsABC Transposase to insert Transposon randomly into the DNA target. The donor: target DNA mass ratio of 1:4 was used according to the manufacturer instructions. The number of isolated plasmids for sequencing after insertion of the Transprimer into the target plasmid was 25. This number was calculated according to the manufacturer instructions and it assumes a 5-fold depth of coverage.

For plasmid pB1 insertion of a ≅1699 bp's transposon-insert at position 973 bp downstream of the multiple-cloning site of the vector used completely eliminated the β-galactosidase activity indicating that the start codon was positioned between the vector MCS (multiple cloning site) and the transposon site, whereas insertion of the insert at position 841 bp downstream of the MCS led to the formation of an active β-galactosidase indicating that the start codon exists between 841 bp and 973 bp downstream of the MCS. The enzyme activity was eliminated completely with insertion of the insert at a position 3565 bp downstream of the MCS indicating that the stop codon is downstream of this position. Moreover insertions at positions 1239 bp, 1549 bp, 1683 bp, 1832 bp, 2108 bp, 2189 bp, 2270 bp, 2340 bp, 2414 bp, 2574 bp, 2648 bp, 2734 bp, 2807 bp and 3410 bp completely eliminate the enzymatic activity.

The sequencing reaction mix contained approximately 400-600 ng plasmid DNA, 3.2 pmol of primer solution and 4 μl of BigDye Terminator solution.

Open Reading Frame Identification

The open reading frame (ORF) of B1 was located by using the ORF finder from NCBI. The bacterial genetic code was used and the frame length was determined to be 100 bp. The nucleotide sequence was translated in all six possible frames and an open reading frame of 1052 amino acids encoding a putative β-galactosidase was identified (The translation is shown in FIG. 2).

EXAMPLE 2

Synthesis With the β-Galactosidase Cloned Enzyme Isolated From *Bifidobacterium bifidum* NCIMB 41171 in *E. coli* Host (StrainDH5a)

The following described synthesis, unless otherwise stated, was performed with the whole *E. coli* DH5a host cells after treatment of the *E. coli* biomass (collected by centrifugation at 10,000 g) with toluene at a concentration of 2000 ppm in order to increase cell permeability and also to render the cells non-viable by destroying their cytoplasmic membrane. The *E-coli* biomass was prepared as described in Example 1 under "*E coli* strains".

Synthesis With Cloned Enzyme

Synthesis with β-galactosidase was performed at a substrate concentration of 40% (w/w) initial lactose concentration. The synthesis solution was prepared in 0.1 M phosphate buffer at pH 6.8 (or 0.1M citrate buffer pH 6.2 or potassium phosphate buffer pH 6.8)). Synthesis was performed at 40° C. in shaking waterbath at 150 rpm. The pH optimum for the specific enzyme was chosen based on activity measurements (using o-nitrophenyl-β-D-galactopyranoside as substrate) of a specific enzymatic preparation at varying pH values.

For galactooligosaccharide synthesis 5 ml of an *E. coli* DH5a cell suspension (with an activity of 2.2 U/ml) were centrifuged (at 10,000 g) to collect the biomass and the supernatant was discarded. This biomass was re-suspended with 10 g of 40% (w/w) substrate solution in order to perform the synthesis.

Figure 3:
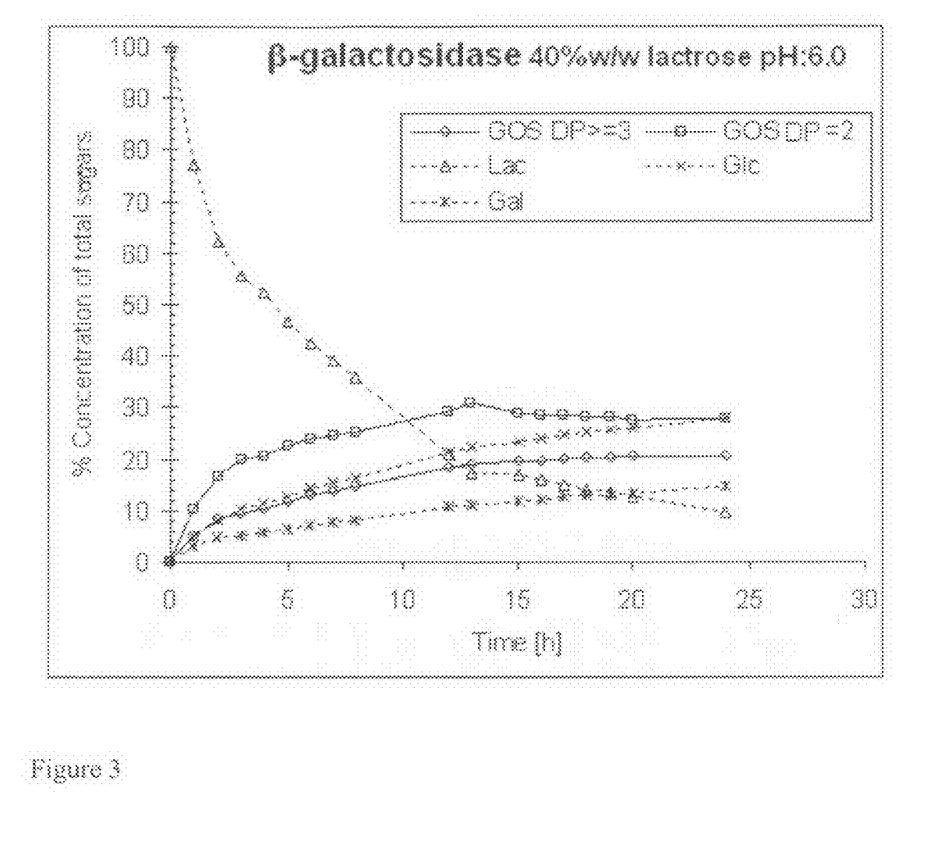
FIG. 3 is a graph showing the time course reaction during galactooligosaccharide synthesis with the β-galactosidase and 40% (w/w) lactose in 0.1M phosphate buffer at pH 6.0 as substrate.
Figure 4:
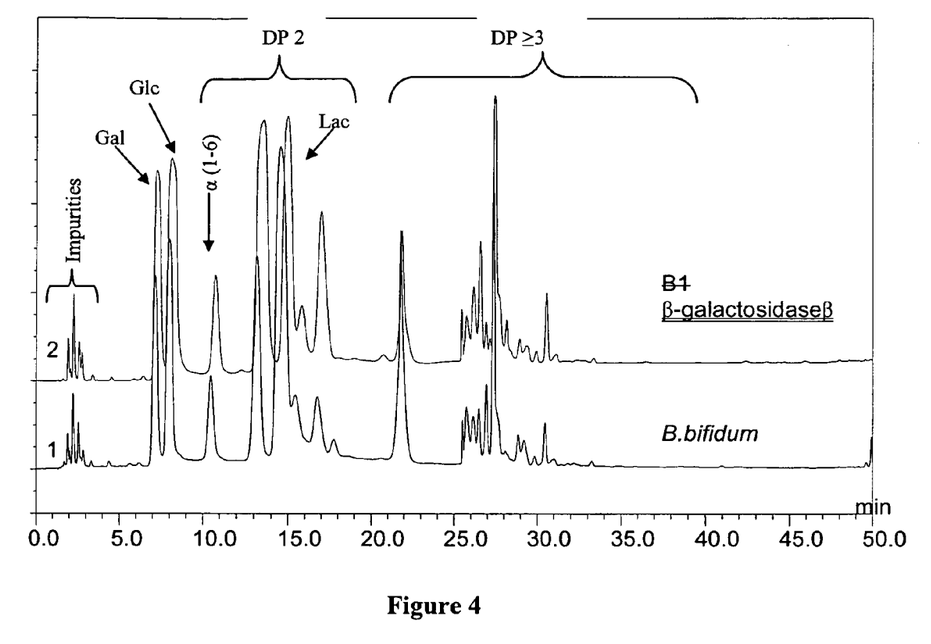
FIG. 4 shows a high performance anion exchange chromatogram of the galactooligosaccharide mixture synthesized by the β-galactosidase from B. bifidum NCIMB 41171 using 40% (w/w) lactose in 0.1M phosphate buffer at pH 6.0 as substrate. (Glc=glucose, Gal=galactose, Lac=lactose, α (1-6) galactobiose, DP=degree of polymerisation).

The concentrations of the different sugars present in the mixture during synthesis are shown in FIG 3. High performance anion exchange chromatography coupled with pulsed amperometric detection (HPAEC-PAD) chromatograms of galactooligosaccharide mixtures synthesized by the β-galactosidase cloned from *B. bifidum* NCIMB 41171 are shown in FIG 4. The galactooligosaccharide mixture sugar concentrations at the optimum synthesis time point are shown in table 1.

TABLE 1

Carbohydrate composition of galactooligosaccharide synthesis at 40% (w/w) initial lactose concentration at the time point where maximum oligosaccharide concentration was observed.

| Synthesis Init. Subst. % (w/w) | GOS DP ≧ 3 | GOS DP = 2 | Lac | Glc | Gal |
|---|---|---|---|---|---|
|  |  | Concentration (% of total sugars) |  |  |  |
| 40 | 20.45 | 27.64 | 12.73 | 25.90 | 13.28 |

Lac: Lactose, Glc: glucose, Gal: galactose, DP: degree of polymerisation

The invention claimed is:

1. An isolated enzyme encoded by the DNA sequence of SEQ. ID NO:1.

2. An isolated enzyme comprising the amino acid sequence of SEQ. ID NO: 2.

3. An isolated β-galactosidase having the amino acid sequence of SEQ. ID NO:2.

* * * * *

SEQUENCE LISTING

<160> NUMBER OF SEQ ID NOS: 2

<210> SEQ ID NO 1
<211> LENGTH: 7281
<212> TYPE: DNA
<213> ORGANISM: Bifidobacterium bifidum
<220> FEATURE:
<221> NAME/KEY: gene
<222> LOCATION: (1)..(7281)

<400> SEQUENCE: 1

| | | | | | | |
|---|---|---|---|---|---|---|
| ggatccggtg | aacgcgccga | gcgcggtgta | cgtgctgcgc | tcgtgcgagt | cggaggagat | 60 |
| cgcggggatc | atgccccagt | aggagatgtc | gcgcagcgag | tagatcacgt | cgagcaggat | 120 |
| gaacacgatg | acgaacagga | ccatgaacac | gccggtgttc | acatccacga | ggccgaacag | 180 |
| gccggtgaac | accatgatca | gcaggatgcc | aggcacgatg | ccgccaatga | actgccacgg | 240 |
| gcggaaccgg | ccccagcggg | tgttcgtgtt | gtccacgagg | ttgccgagca | gcgggtcgag | 300 |
| aaagatctcc | gcgatgcgga | tgaccaccac | gagtccggtg | atcaccgcga | tgaggcgttt | 360 |
| ggcaagcgtc | ttgtccacgt | cgatgaacag | cgcggtggtc | acgaacgtga | tgaagaacgt | 420 |
| gctcattgtg | ttgtagaacg | cggcctggcc | caggttaccg | aatgcgtatg | cgatcttctg | 480 |
| acccgtgttc | cgcgtgggct | gcggccttcc | ggtcgtttcc | gtgtgttgtg | tggtggatcc | 540 |
| gctcatggtg | tggtggcctc | cttgcgacct | gtaaagaatc | cgtgcgcgtg | aaccgctccg | 600 |
| atcccgcaaa | gcgtgagtat | agaactttct | tgaaaaagta | gaaaactata | ccgcgtgtcg | 660 |
| caaatcatgc | caacgttctg | caaccggcac | tccgtgtgga | tgagtaaggt | ttgaagcctg | 720 |
| cttgatgtgc | ttgaatctta | agaaatccac | gtattctgca | tgttcaggc | cttgtgccgc | 780 |
| gaaatgctgg | aaagaatttg | cgcaatcaag | taacaatatt | tatccttgtt | gtacaaggaa | 840 |
| cccgattcaa | cgaggttccc | tcactgcggc | ggcaacgacg | cgacgcaatc | cgatgcgaaa | 900 |
| gcgaggacat | catgaacaca | accgacgatc | agcggaagaa | cggcgatccg | atcgtctccc | 960 |
| cgtccatacc | gacgacggca | tggctcgccg | accgcgcgt | gtacgcggtt | caccggctcg | 1020 |
| acgcccattc | cgatcatgcg | tgctggtctc | gctccccagt | cgacggcgag | agcacgaatc | 1080 |
| tcaggcagag | ccttgacggc | gaatggcggg | tccgcgtcga | gacggcgccg | acgggccgtt | 1140 |
| tccccgatgg | gacgagcgac | gggccggact | ggatcagcga | cgtgtcgcct | ctgttcgccg | 1200 |
| cgcccggatt | cgacgattcg | tcgttctcac | gcgtgcaggt | gccctcgcat | ctggagactg | 1260 |
| cggggctgct | tgccccgcag | tacgtgaacg | tgcagtaccc | atgggacgga | catgaggacc | 1320 |
| cgaaggcccc | ggccatcccc | gagcatggcc | atgtggcggt | ctaccggcgc | gagttcgacg | 1380 |
| cggatggcga | agtcgcccag | gccgtgcgcg | aagggcgccc | ggtgacgctt | accttccagg | 1440 |
| gcgcggccac | agccatctac | gtgtggctca | acggctcgtt | cgttggctac | gccgaggact | 1500 |
| ccttcacgcc | cagcgagttc | gacgtgacgg | acgcgatcaa | ggtggacggc | aacgtgctgg | 1560 |
| cggtcgtctg | ctacgagtat | tcgagcgcga | gctggttgga | ggatcaggac | ttctggcgtc | 1620 |
| tgcacggcct | gttccgctcc | gtcgaactca | acgcgaggcc | cgccgccac | atcgccgacc | 1680 |
| tccatgccga | cgccgactgg | gatctcgcca | catcaagggg | ttcgctctcg | ctggatgtgc | 1740 |
| tgatcgacgg | tgccgcgaac | gccgcgacgg | tcgacttcg | actgtgggac | aagaacggca | 1800 |
| ccatcgtctg | gcacaccgcc | acgaaagcgg | acggaacgct | gcacgccgag | gccgagatcg | 1860 |
| atgacgcggc | gccatggagc | gccgaacgcc | ccgacctgta | cgagctatcc | gtcacccgc | 1920 |
| tcgacgcgga | cggcaaggtc | ctggagaccg | ctcgcactcg | catcggcttc | cggcatgtgg | 1980 |

-continued

| | |
|---|---|
| ccatcgagga cggcatcctc aagctcaacg gcaagcgcct cgtgttccgt ggcgtcaacc | 2040 |
| gccacgagtt cgactgccgg cgcggccggg ccatcaccga agaggacatg ctgtgggaca | 2100 |
| tccgcttcat gaagcgccac aacatcaacg cggtgcgcac ctcgcactat ccgaaccagt | 2160 |
| cgcgctggta cgagctgtgc gacgaatacg gcatctacct gatcgacgag accaatctgg | 2220 |
| agacccatgg cagctggaac agccccggcg acatccccgt gggaacctcc gtccccggtg | 2280 |
| acgacgaggc ctggctgggc gcgtgcatcg accggctgga cagcatgatc ctgcgcgacc | 2340 |
| gcaaccatcc cagcgtgctc gtctggtcgc tgggcaacga atcctacgcg ggcgaagtcc | 2400 |
| tcaaggccat gagcgcgcac gcgcaccggc ttgatccggg tcgtcccgtc cactacgaag | 2460 |
| gtgtcaactg gaaccatgcc tacgacggga tcagcgactt cgaaagccgt atgtacgcca | 2520 |
| agccggccga gatccaagac tggctcgaac acgcgacga acggggcgag gcgagcaagc | 2580 |
| cgttcgtcag ctgtgagtac atgcatgcca tgggcaactc gtgcggcggt ctgagcgagt | 2640 |
| tcatcgacct cgaacggtac gagcgctact ccggcgggtt catctgggat tacatcgacc | 2700 |
| aggggctcgt ccagcgtctg cccgacggga gcgaacgcct cagcgtcggc ggagaatggg | 2760 |
| gcgaccgtcc aaccgactac gaattcgtgg gcaacggcat cgtgttcgcc gaccgcacgc | 2820 |
| ccagccccaa ggcgcaggag gtcaagcagc tgtattcgcc ggtcaagctc gccccgacg | 2880 |
| ggcacggcgt gaccatcgag aaccgcaacc tgttcgccgg caccgacggc tacgtgttcg | 2940 |
| ccgcacggct cctcgaagac gggcatgaga tctggcatgc cgactaccgt ttcgacgtgg | 3000 |
| ccgcaggaga tacccaacac catgacatcg ccttcccgga catcgacgcg gacgggata | 3060 |
| cgcgcgaagt cacctacgag gtcgatctcc tgctcgccga agccaccgca tgggcgccgg | 3120 |
| ccggctacga gctcgcgttc ggccaactca ccggcacgct caaccccgaa caggacatca | 3180 |
| ccgagaccag ccatgacgac gacggccgcg caactcgcac gctcagccga tggaacgccg | 3240 |
| gcatccgccg cgacgacgag gaaattctcc tgtcacgcac tcaggaggc atcgtctcct | 3300 |
| ggaagcgcga cgaccgggaa atggtcatcc gtcgccccga actcgtcacg ttccgcccat | 3360 |
| tgaccgacaa cgatcgcggt aaccattccg gtttcgaccg tgccgcatgg ttcgcggccg | 3420 |
| gccgatacgc catcgtaacc gaaacgaaaa tccatgaaag cgatgacggt ctcgtagcgg | 3480 |
| aataccagta cgaacttgcc gatccgaacc acacgcccgt gtccgtcact taccatgtca | 3540 |
| actccgatat gcgtatgcaa ctgaccgtcg aatacccccgg gaacgccact gacatggcca | 3600 |
| gtctgcccgc gttcggtatc gaatgggagc tgcccggcga atacgatcgt ctgcgctact | 3660 |
| acggccccgg ccccgaggag acctaccgcg accgtaagca gggcggcaag ctcggcatct | 3720 |
| gggacgccac cgcgaaggcg agcatggcgc cgtatctcat ggtgcaggaa accggcagcc | 3780 |
| acgaggacgt ccgctggctc gaagccaccg acatccaagg ccacggattg cgcgtcaccc | 3840 |
| aacgcggcga ccgtcacttc acggccagcc tgctgccctg aaacacctac acgatcgagg | 3900 |
| ccgcgcgccg ccacgaggac ctgcccaaac cgcgccacaa ctacctgcgc ctgctcgcgg | 3960 |
| cccagatggg cgtcggtgga gacgactcct ggggagcccc cgtccacacg gcctaccagc | 4020 |
| tgcccgccgg caggccgctc accctcgacg tgaacctcga actcatctga ccggcaacgg | 4080 |
| gcggcggcat gcaccaccat gccgccgcg gccccgccta cgacgcggcg atcgaggcca | 4140 |
| cgggcgctgc ggccgcggac ggcaccggcg aggaggcgtt cgagcgcgcc ggccacgcgg | 4200 |
| tccacggcac caccccgcca gtcctctcgc tcatcaccaa cccgatggac gtgatctgcc | 4260 |
| gcaacatccg caccgtgcgc gagaagatgg caacccgccc cgacatcctc ggctgccacc | 4320 |
| tcgaaggccc gttcctcgcc ctcaagtgca agggcgcgca cgattcgaac tgcctcaaag | 4380 |

```
acccgatgcc cgaactcatg gaccgcatgc tcgacgcctc gggcgccgac ctcgccgccg   4440
gcaagctcgg gtgcatccgc cagatcacca tctcgacccc accgactgga ccgcccaaca   4500
cgtctggtgc gccggccgcc aggtggagta aactccttcc agcaaaatcg acgccggtgc   4560
cgcccgtctc gagacgacgt cttacgcctg aggaacgaag cttgcgcgcg caccagttc    4620
ggtcgtcagc aggatgtgac gacgcacccg ccgctcatgc ttcaacccat cgatcagggt   4680
ggagaacgcc atgcgggcca actcccttg atcgatcgca tacgaactca gcggcggcga    4740
cgtgtaccgg gcgatcgact ggttgttcac actcaccacg gccaactcgt cgggaacctc   4800
cacgcgcagt gcgttcaacg cctgcaacgc ccccaccgca agcacgtcgg cggccacgat   4860
caaaccatcg ggcatgctgc cggcctcacg atggtcagcc accaactgct ccgcgagacg   4920
atagccgttc tccacggtga acgtgccgga cgaatacacc aatccgtccg tttccaatcc   4980
cagatgcgcg gcccactgac ggaacgacag ctcgcgaatg tcctcgggat agtcatgcat   5040
gcccatgatg ctgcccacgc cgccgagaaa cgcgatatga ctgcggcccg ccgcgatcat   5100
cgcgtccaag gcgtccagca tcgtctgcga cagatcggga cacacggagt cgaacaggcg   5160
cggcgccgga ttcgtgtcga tgcacacgcc atgcgggagc accatatgca gggctcgcag   5220
gtccgcttcg ggaaacaccg tggctcccac ggtgatgaac ccatcaaact ccgttgcgcg   5280
ttccgtcaac tcgtgtatgg acaacgtgag ctggtccaat ccaacgact ccgcacgctc     5340
cgcaagaacc ttccgcagat cggcgaagta cgcgtcctgc aattcctccc cggacggagg   5400
cgcatccaac accgcgatcg cgggacggaa cacgttgcga tacccatct cctcgcacac     5460
gcgcaacaca cgccgacgcg tctcctcctt gatggagaac gacgggtcgt tcaacaagcg   5520
tgacaccgtg ctctgcgaca ccccggcccg tccttgagcg tggccatgac                5580
atcctccccg caaactttag taaagggttt tactacagca taacccggga aggcggggtt   5640
agcggcattg gcggcgtgga agtttaccca tgactggtag actgcacatg tcccggcaat   5700
aggggcaatg catagggggg tggcgggcat gtgcagcaac attcccgtca ccttacgatt   5760
cttatagcgt gtcaggtaaa agaattatga ttctcaatcc accttccggc cgcgcctgca   5820
gactcaaatg gccatgatgc atagcgacaa tctctcgcac tatggataaa cccaatccgt   5880
gatgaggtga tgcagatccc acatgcgtat ttatcctatt atcctcccct ctgttaaaag   5940
gtgacaggaa atcatctatc ctcgtatcgg aaagatccat gccggtattg gatatgtcta   6000
tcgcaatgca ggactcgcct tcgtattgcc tgtcgttggc taagtttatc catacatgtg   6060
gttgagccgc acgattatgc tgaatggcat tcgtaataag gtttgcaatc atctgtctaa   6120
ttagcagacc atcggctagg atatatgcat tctccagatt ggtatgtact tgaactctat   6180
ctccgataag ttccatatt tcctgaagaa cattgcgaat gatctcagct acattaactc     6240
ggctaagatc agctcggttt aattgctgaa cttcgacaa ttcgagcaga tgattgacga     6300
tttcaacccc agcatgattt gaagccaaag ccttttcgac gaaaggtctg caacgctcat   6360
cgaaaagctg gttgtgcagc ggaatctcca atgcggccga agtggccgca agtggatttt   6420
ttaactcatg tgacgcatcg gcgataaatt ccttttcccg actgattgcg ctgttgagat   6480
cctttaacat gaggttgtat gcggatgcaa tagtgtacgc ctcgtcgttt tcatatggaa   6540
taacgatagg ttgcctttcc aatccagcgt cggacgcgat aatctgagag ccacactat    6600
tgattcttcg ttgtgtccta gtggcgataa tccaagttat tcctccagat aatatgccga   6660
aaacaatgat gggggctatg cttaccgcca atatcagatc ccgggatttt atgtctcctt   6720
gttccatagt tagcgttaaa gcatccttac cggagtcata cccggcagaa acgtaatcct   6780
```

-continued

```
taccggagtc aggaggaatg gcttgcgaat tcaaactatg ttgttcatcg gcatcttctg    6840
cctgagtaaa agatttattt acggtcactg tttccagttg ccggttcacg acataatatg    6900
tcatggcggt caccactccg gtaagcatga agaacacgat gacgatcgtg gtgaccaatc    6960
ttcttcttgt agaccactga aacgtaaaac gcagtttcgg atggctggaa tggctcccat    7020
tcgacgaagg atattcaggc tttttcatga tatgcgatat ccttgtccgg gaacggtttc    7080
aatgaaatca gtgattccga ttttcgtgcg aatcgcatag attgtggtct tgacgattcc    7140
tctcgtatga gcgtgatcat cctgccaaat ctcacgatat agacattccg cactaatcac    7200
cgcacctcgc gcctcaatca gcgtcctcaa tacggcaagt tctcgtttcc caaactttag    7260
ttctgcaccg cgaaccgtga t                                              7281
```

<210> SEQ ID NO 2
<211> LENGTH: 1052
<212> TYPE: PRT
<213> ORGANISM: Bifidobacterium bifidum
<220> FEATURE:
<221> NAME/KEY: PEPTIDE
<222> LOCATION: (1)..(1052)

<400> SEQUENCE: 2

```
Met Asn Thr Thr Asp Asp Gln Arg Lys Asn Gly Asp Pro Ile Val Ser
1               5                   10                  15

Pro Ser Ile Pro Thr Thr Ala Trp Leu Ala Asp Pro Arg Val Tyr Ala
            20                  25                  30

Val His Arg Leu Asp Ala His Ser Asp His Ala Cys Trp Ser Arg Ser
        35                  40                  45

Pro Val Asp Gly Glu Ser Thr Asn Leu Arg Gln Ser Leu Asp Gly Glu
    50                  55                  60

Trp Arg Val Arg Val Glu Thr Ala Pro Thr Gly Arg Phe Pro Asp Gly
65                  70                  75                  80

Thr Ser Asp Gly Pro Asp Trp Ile Ser Asp Val Ser Pro Leu Phe Ala
                85                  90                  95

Ala Pro Gly Phe Asp Asp Ser Ser Phe Ser Arg Val Gln Val Pro Ser
            100                 105                 110

His Leu Glu Thr Ala Gly Leu Leu Ala Pro Gln Tyr Val Asn Val Gln
        115                 120                 125

Tyr Pro Trp Asp Gly His Glu Asp Pro Lys Ala Pro Ala Ile Pro Glu
    130                 135                 140

His Gly His Val Ala Val Tyr Arg Arg Glu Phe Asp Ala Asp Gly Glu
145                 150                 155                 160

Val Ala Gln Ala Val Arg Glu Gly Arg Pro Val Thr Leu Thr Phe Gln
                165                 170                 175

Gly Ala Ala Thr Ala Ile Tyr Val Trp Leu Asn Gly Ser Phe Val Gly
            180                 185                 190

Tyr Ala Glu Asp Ser Phe Thr Pro Ser Glu Phe Asp Val Thr Asp Ala
        195                 200                 205

Ile Lys Val Asp Gly Asn Val Leu Ala Val Val Cys Tyr Glu Tyr Ser
    210                 215                 220

Ser Ala Ser Trp Leu Glu Asp Gln Asp Phe Trp Arg Leu His Gly Leu
225                 230                 235                 240

Phe Arg Ser Val Glu Leu Asn Ala Arg Pro Ala Ala His Ile Ala Asp
                245                 250                 255

Leu His Ala Asp Ala Asp Trp Asp Leu Ala Thr Ser Arg Gly Ser Leu
            260                 265                 270
```

```
Ser Leu Asp Val Leu Ile Asp Gly Ala Ala Asn Ala Ala Thr Val Asp
    275                 280                 285

Phe Ala Leu Trp Asp Lys Asn Gly Thr Ile Val Trp His Thr Ala Thr
290                 295                 300

Lys Ala Asp Gly Thr Leu His Ala Glu Ala Glu Ile Asp Asp Ala Ala
305                 310                 315                 320

Pro Trp Ser Ala Glu Arg Pro Asp Leu Tyr Glu Leu Ser Val Thr Leu
                325                 330                 335

Leu Asp Ala Asp Gly Lys Val Leu Glu Thr Ala Arg Thr Arg Ile Gly
            340                 345                 350

Phe Arg His Val Ala Ile Glu Asp Gly Ile Leu Lys Leu Asn Gly Lys
        355                 360                 365

Arg Leu Val Phe Arg Gly Val Asn Arg His Glu Phe Asp Cys Arg Arg
370                 375                 380

Gly Arg Ala Ile Thr Glu Glu Asp Met Leu Trp Asp Ile Arg Phe Met
385                 390                 395                 400

Lys Arg His Asn Ile Asn Ala Val Arg Thr Ser His Tyr Pro Asn Gln
                405                 410                 415

Ser Arg Trp Tyr Glu Leu Cys Asp Glu Tyr Gly Ile Tyr Leu Ile Asp
            420                 425                 430

Glu Thr Asn Leu Glu Thr His Gly Ser Trp Asn Ser Pro Gly Asp Ile
        435                 440                 445

Pro Val Gly Thr Ser Val Pro Gly Asp Asp Glu Ala Trp Leu Gly Ala
    450                 455                 460

Cys Ile Asp Arg Leu Asp Ser Met Ile Leu Arg Asp Arg Asn His Pro
465                 470                 475                 480

Ser Val Leu Val Trp Ser Leu Gly Asn Glu Ser Tyr Ala Gly Glu Val
                485                 490                 495

Leu Lys Ala Met Ser Ala His Ala His Arg Leu Asp Pro Gly Arg Pro
            500                 505                 510

Val His Tyr Glu Gly Val Asn Trp Asn His Ala Tyr Asp Gly Ile Ser
        515                 520                 525

Asp Phe Glu Ser Arg Met Tyr Ala Lys Pro Ala Glu Ile Gln Asp Trp
    530                 535                 540

Leu Glu His Gly Asp Glu Arg Gly Glu Ala Ser Lys Pro Phe Val Ser
545                 550                 555                 560

Cys Glu Tyr Met His Ala Met Gly Asn Ser Cys Gly Gly Leu Ser Glu
                565                 570                 575

Phe Ile Asp Leu Glu Arg Tyr Glu Arg Tyr Ser Gly Gly Phe Phe Trp
            580                 585                 590

Asp Tyr Ile Gly Gln Gly Leu Val Gln Arg Leu Pro Asp Gly Ser Glu
    595                 600                 605

Arg Leu Ser Val Gly Gly Glu Trp Gly Asp Arg Pro Thr Asp Tyr Glu
610                 615                 620

Phe Glu Gly Asn Gly Ile Val Phe Ala Asp Arg Thr Pro Ser Pro Lys
625                 630                 635                 640

Ala Gln Glu Val Lys Gln Leu Tyr Ser Pro Val Lys Leu Ala Pro Asp
                645                 650                 655

Gly His Gly Val Thr Ile Glu Asn Arg Asn Leu Phe Ala Gly Thr Asp
            660                 665                 670

Gly Tyr Val Phe Ala Ala Arg Leu Leu Glu Asp Gly His Glu Ile Trp
        675                 680                 685

His Ala Asp Tyr Arg Phe Asp Val Ala Ala Gly Asp Thr Gln His His
    690                 695                 700
```

```
Asp Ile Ala Phe Pro Asp Ile Asp Ala Asp Gly Asp Thr Arg Glu Val
705                 710                 715                 720

Thr Tyr Glu Val Asp Leu Leu Ala Glu Ala Thr Ala Trp Ala Pro
            725                 730                 735

Ala Gly Tyr Glu Leu Ala Phe Gly Gln Leu Thr Gly Thr Leu Asn Pro
            740                 745                 750

Glu Gln Asp Ile Thr Glu Thr Ser His Asp Asp Asp Gly Arg Ala Thr
            755                 760                 765

Arg Thr Leu Ser Arg Trp Asn Ala Gly Ile Arg Arg Asp Asp Glu Glu
            770                 775                 780

Ile Leu Leu Ser Arg Thr Gln Gly Gly Ile Val Ser Trp Lys Arg Asp
785                 790                 795                 800

Asp Arg Glu Met Val Ile Arg Arg Pro Glu Leu Val Thr Phe Arg Pro
                805                 810                 815

Leu Thr Asp Asn Asp Arg Gly Asn His Ser Gly Phe Asp Arg Ala Ala
                820                 825                 830

Trp Phe Ala Ala Gly Arg Tyr Ala Ile Val Thr Glu Thr Lys Ile His
                835                 840                 845

Glu Ser Asp Asp Gly Leu Val Ala Glu Tyr Gln Tyr Glu Leu Ala Asp
850                 855                 860

Pro Asn His Thr Pro Val Ser Val Thr Tyr His Val Asn Ser Asp Met
865                 870                 875                 880

Arg Met Gln Leu Thr Val Glu Tyr Pro Gly Asn Ala Thr Asp Met Ala
                885                 890                 895

Ser Leu Pro Ala Phe Gly Ile Glu Trp Glu Leu Pro Gly Glu Tyr Asp
                900                 905                 910

Arg Leu Arg Tyr Tyr Gly Pro Gly Pro Glu Glu Thr Tyr Arg Asp Arg
                915                 920                 925

Lys Gln Gly Gly Lys Leu Gly Ile Trp Asp Ala Thr Ala Lys Ala Ser
930                 935                 940

Met Ala Pro Tyr Leu Met Val Gln Glu Thr Gly Ser His Asx Asp Val
945                 950                 955                 960

Arg Trp Leu Glu Ala Thr Asp Ile Gln Gly His Gly Leu Arg Val Thr
                965                 970                 975

Gln Arg Gly Asp Arg His Phe Thr Ala Ser Leu Leu Pro Trp Asn Thr
                980                 985                 990

Tyr Thr Ile Glu Ala Ala Arg Arg His Glu Asp Leu Pro Lys Pro Arg
            995                 1000                1005

His Asn Tyr Leu Arg Leu Leu Ala Ala Gln Met Gly Val Gly Gly
        1010                1015                1020

Asp Asp Ser Trp Gly Ala Pro Val His Thr Ala Tyr Gln Leu Pro
        1025                1030                1035

Ala Gly Arg Pro Leu Thr Leu Asp Val Asn Leu Glu Leu Ile
        1040                1045                1050
```